United States Patent [19]

Dorman

[11] 4,045,384

[45] Aug. 30, 1977

[54] METHOD FOR FORMING AN AMIDE BOND BETWEEN A LATEX AND PROTEIN

[75] Inventor: Linneaus C. Dorman, Midland, Mich.

[73] Assignee: The Dow Chemical Company, Midland, Mich.

[21] Appl. No.: 708,232

[22] Filed: July 23, 1976

[51] Int. Cl.$^2$ ............................................. C08L 89/00
[52] U.S. Cl. ................................. 260/8; 260/112 R; 424/88; 424/100; 424/105; 424/177
[58] Field of Search .............................. 260/8; 424/12

[56] References Cited

U.S. PATENT DOCUMENTS

| | | | |
|---|---|---|---|
| 3,700,609 | 10/1972 | Tregear et al. | 260/8 |
| 3,839,153 | 10/1974 | Schuurs et al. | 424/12 |
| 3,857,931 | 12/1974 | Hagar | 260/8 |
| 3,951,748 | 4/1976 | Devlin | 424/12 |
| 3,969,287 | 7/1976 | Jaworek et al. | 260/8 |

*Primary Examiner*—Edward M. Woodberry
*Attorney, Agent, or Firm*—James W. Ambrosius

[57] ABSTRACT

A method of linking a protein to a carboxylated latex by an amide bond which comprises the steps of forming an active ester latex, dialyzing the active ester latex, and coupling the latex to a protein such as an antibody or an antigen.

6 Claims, No Drawings

METHOD FOR FORMING AN AMIDE BOND BETWEEN A LATEX AND PROTEIN

BACKGROUND OF THE INVENTION

The antigen-antibody reaction is the basis for all immunological test methods. Special proteins called antibodies are produced by an animal in response to the presence of an antigen, that is a foreign protein, in the body fluids of the animal. This normal body response to a foreign protein has lead to the development of a number of techniques which are used to diagnose various human and animal diseases or disorders. Immunological test methods may also be used to detect pregnancy. In vitro tests for the presence of a suspected antigen or antibody in a body fluid are carried out by adding the immunological counterpart to a vial of the body fluid, i.e. add antigen if the test is for the presence of antibody or add antibody if the test is for the presence of antigen. If the suspected protein is present the resulting antigen-antibody reaction is generally manifested by precipitation or agglutination of the antigen-antibody complex. As used herein the term body fluid refers to urine, serum, plasma, or the like.

In some instances the antigen-antibody complex is slow to form and the particles that are formed are too small to be observed with certainty. In such cases, detectability of the antigen-antibody reaction can be improved by utilizing a carrier. When the antigen or antibody is coated on the surface of a carrier the reaction with the immunological counterpart produces a visible mass or agglutant. The proteinic antigen or antibody may be adsorbed onto the surface of carriers such as erythrocytes, bacterial cells, bentonite, polystyrene latex particles, anionic phenolic resins, or finely divided diazotized amino cellulose. It has been found however, that chemical binding of the antigen or antibody molecule to the carrier is superior to physical adsorption. U.S. Pat. No. 3,857,931 teaches that proteinic antigens or antibodies can be chemically bound to a polymer latex carrier having surface carbonyl groups. Amide bonds form between the protein and carboxylated latex in the presence of a water-soluble carbodiimide coupling agent.

Mechanistically, the carbodiimide is believed to react with the carboxyl groups on the latex to form a transient activated intermediate acylisourea which in turn reacts with the amino groups on the protein to form a stable amide board affixing the protein to the latex surface. See DeTar, D. F., et al., *J. Amer. Chem. Soc.* 88, 1024 (1966).

A disadvantage of processes used by the prior art is the inability to control the undesirable and indiscriminate reaction of the carbodiimide with the carbonyl groups that are also present on the proteinic antigens and antibodies. Thus, the activated carbonyls on the protein itself can react with the amino group of the protein resulting in intra- or inter-protein crosslinking. This can result in conformational or structural distortion of the protein molecule which in turn can effect immunochemical sensitivity. These side reactions are especially acute when the protein contains relatively large amounts of aspartic and glutamic acid in the protein chain since these amino acids contain free carboxyl groups. An example of such a protein is human chorionic gonadotropin, hereafter called HCG, which has an isoelectric point of 2.95, indicative of a high negative charge.

A number of immunological tests have been developed for the detection of HCG in urine or serum. HCG is a glycoprotein with a molecular weight of about 27,000 produced by the chorionic tissue of the placenta during pregnancy. Systems using HCG have been used to detect pregnancy. During pregnancy this hormone governs the production and secretion of progesterone by the corpus luteum. HCG is also produced in large quantities by hydatidiform moles, choriocarcinomas, and some tumors of the testis. Low levels of HCG have also been found by radioimmunoassay in the sera of patients with various nontrophoblastic neoplasms. Various agglutination techniques have been used to test for the presence of HCG.

Agglutination testing for HCG may be performed by either the indirect or the direct technique. In the indirect technique the clinical sample is mixed with HCG antibody at a dilution that will be completely bound by one or more I.U./ML HCG. After an initial incubation period an indicator system consisting of HCG bound to a particulate carrier (latex or red cells) is added to the mixture. If HCG is present in the clinical sample the HCG antibody will not be available to react with the HCG-carrier complex and there will be no agglutination, thus, absence of agglutination is a positive test for HCG. If, on the other hand, HCG is not present in the clinical sample the HCG antibody will react with the HCG-carrier complex causing agglutination of the indicator system. This is a negative test for HCG in the clinical sample. In the direct technique HCG antibody bound to the carrier reacts directly with the HCG in the clinical sample and there is no need for an intermediate incubation step. Thus, in the direct technique agglutination indicates a positive test for HCG in the clinical sample.

Chemical coupling of protein to latex particles by means of an amide bond is discussed in *Am. Review of Biochemistry*, 35 (II), 896 (1966) and in Ohno, Y. *Water-Insoluble Acrylic Polymer Derivatives of Enzymes and Antigens*, The Univ. of Wisc. (1967). Chemical coupling of a protein to a carrier for use in immunological diagnosis is shown in U.S. Pat. Nos. 3,533,310; 3,775,536; and 3,879,262.

SUMMARY OF THE INVENTION

The present invention is directed to a novel process for forming an amide linkage between a protein such as an antigen or antibody and a latex. The term latex as used herein refers to an aqueous colloidal dispersion of a water insoluble carboxyl containing polymer. Chemical coupling of the protein to the latex surface is accomplished in the process that is the subject of this invention in three distinct steps. The first step involves the formation of an active ester at the latex surface through the reaction of a water solubilizing N-hydroxy compound, a water-soluble carbodiimide, and the latex. The reaction mixture is cleaned to remove the unchanged reactants, in particular any unchanged carbodiimide and by-products, by dialysis, centrifugation, or ultrafiltration. Following removal of unchanged reactants an aqueous buffered solution of protein is added to the latex active ester along with some additional N-hydroxy compound. This results in the formation of amide bonds between the latex carboxylic acid active ester and the amino groups of the protein. The chemistry of this process is summarized in the following equations which shown N-hydroxybenzotriazole as the N-hydroxy compound.

Step 1: Activation

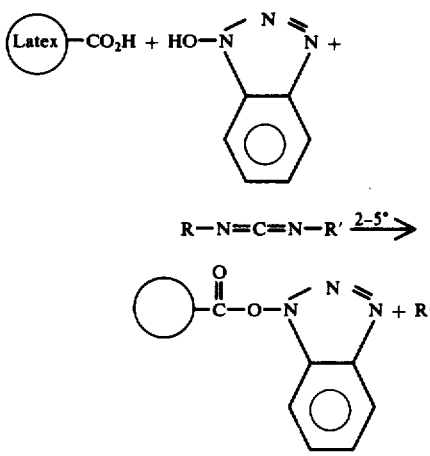

Step 2: Cleaning the Latex

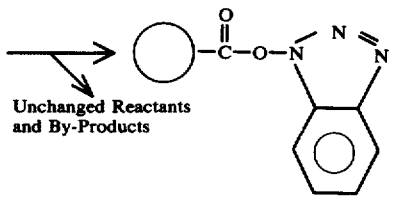

Unchanged Reactants and By-Products

Step 3: Coupling

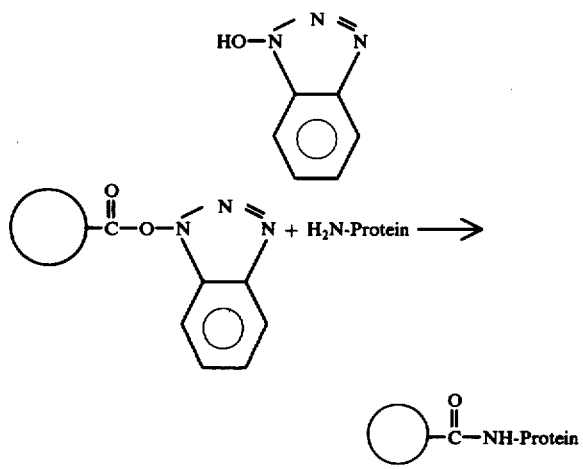

wherein R and R' represent water-solubilizing groups such as cycloalkyl having from 5 to 6 carbon atoms in the ring; alkyl of from 2 to 12 carbon atoms, e.g. ethyl, n-propyl, isopropyl, n-butyl, sec-butyl, isobutyl, tert-butyl, amyl, hexyl, heptyl, octyl, nonyl, decyl, undecyl, and dodecyl; monoarylsubstituted lower alkyl radicals, e.g. benzyl, α- and β-phenylethyl; monoaryl radicals, e.g. phenyl, morpholino, piperidyl; morpholinyl substituted lower alkyl radicals, e.g. ethyl morpholinyl; piperidyl substituted lower alkyl radicals, e.g. ethyl piperidyl substituted lower alkyl radicals, e.g. ethyl piperidyl; di-lower alkylamino; lower alkyl radicals; pyridyl substituted lower alkyl radicals, e.g. α, β, and λ methyl or ethyl pyridyl; acid addition salts; and quaternary amines thereof.

The N-hydroxy compound N-hydroxybenzotriazole is preferred for use in the formation of the active ester. However, other N-hydroxy compound may also be used such as for example substituted derivatives of 1-hydroxybenzotriazole, N,N-dialkylhydroxylamine, 1-hydroxypiperidine, N-hydroxysuccinimide, N-hydroxyphthalimide, or various substituted N-hydroxy-imides (e.g. N-hydroxy-5-norbornene-2,3-dicarboximide). In the process of the present invention the carboxyl groups on the polymer are activated through the formation of an active ester in the absence of protein. This active ester is sufficiently stable to allow removal of any unchanged carbodiimide coupling agent by dialysis, ultrafiltration or centrifugation. The protein, therefore, is added only after the latex has been cleaned which avoids the possibility of unwanted side reactions. This is a distinct advantage over processes known to the prior art.

DETAILED DESCRIPTION OF THE INVENTION

Any carboxylated latex would be suitable for use in the process of the present invention. Examples of specific latex which can be used as a carrier include vinyl acids, acrylic, itaconic, fumaric and other vinyl carboxylic acids capable of being copolymerized with styrene. Likewise, latexes derived from styrene such as for example styrene butadiene acrylic acids and other vinyl carboxamides such as methacylamide would be satisfactory in the practice of this invention.

It has been found that monodispersed latexes having uniform particles sizes are preferred because uniformity of size assures an equal statistical distribution of antigen or antibody molecules on the surface of the latex particles. For a given weight of polymer, the total surface area of the latex will increase with a decrease in the size of the particles and vice versa. Thus, in a latex containing a distribution of various particle sizes the smaller particles will have a greater surface area and consequently more total reaction sites than the larger particles. The unequal distribution of antigen or antibody on the latex particles will lead to unequal agglutination of particles and poorly defined diagnostic results.

Another advantage of using uniform latex particles as diagnostic agents is that they are better suited for instrumental analysis. Particles of the same size will flocculate, agglutinate, or settle at the same rate whereas different sized particles will agglutinate at variable rates. Thus an instrumental method based on the absorption or transmission of light through an agglutinating latex suspension will be more accurate, more reproducible, and easier to standardize and read with uniform latex particles than with latexes having varied particle sizes.

In carrying out Step 1 of the process it is preferred that the amount of water-soluble carbodiimide be equal to the chemical equivalence of the carboxyl groups of the latex. The use of more carbodiimide is inconsequential to the activation process, but may decrease the effectiveness of dialysis in removing unchanged carbodiimide before the coupling Step 3. Use of less carbodiimide will decrease the effectiveness of active ester formation.

The following examples illustrate specific embodiments of the present invention but are not to be construed as a limitation thereon.

EXAMPLE 1

In a siliconized 25-ml round bottomed flask equipped with a thermometer in the sidearm and containing a Teflon®-coated magnetic stirring bar a mixture was prepared containing 5.0 ml (0.45 g polymer, 0.056 mequiv —CO₂H) of monodispersed styrene-methacrylic acid latex solution and 1.0 ml (0.172 mequiv) of N-hydroxybenzotriazole solution [93 mg (0.689 mequiv) dissolved in 1.6 ml of dimethylformamide and diluted to 4 ml with water]. After mixing, the flask was placed in a cold room (where all manipulations were carried out thereafter) at 5° and when the reaction was cooled to this temperature 0.5 ml (0.059 mequiv) of 1-cyclohexyl-3-(2-morpholinoethyl)-carbodiimide metho-p-toluenesulfonate solution (100 mg diluted to 2.0 ml with water 10 min before using) was added dropwise with vigorous stirring to rapidly disperse the carbodiimide solution upon contact with the latex mixture. When the addition was complete a 0.4 ml aliquot was removed from the reaction mixture (approx. 6.5 ml) for analysis. After 3.67 hours of stirring in the cold, the reaction mixture was transferred with rinses to a Dow Mini Beaker® hollow fiber dialyzer cell (stated capacity 8.0 ml) and dialyzed for 1.8 hours against 0.1M NaCl, the dialyzer effluent volume was 232 ml. The reaction mixture (8.3 ml of which 0.4 ml was removed for analysis) was removed from the cell and was further dialyzed in cellophane against 550 ml of 0.1M NaCl for about 16 hr. An aliquot of 0.4 ml was removed for analysis from the dialyzed reaction mixture, 7.9 ml. The balance was transferred to a clean siliconized 25-ml round bottom flask to which was added with stirring a solution of 5000 IU of HCG in 5 ml of pH 8.0 phosphate buffer (I=0.05) containing 0.1M NaCl followed by 0.3 ml (0.052 mequiv) of the N-hydroxybenzotriazole solution. The pH of the resulting mixture, 6.8, was raised to 7.2 by adding 0.5M Na₂HPO₄ dropwise. Polarographic analysis showed that the amount of unchanged carbodiimide present in the reaction at the time the HCG was added amounted to 299 ppm or 0.3 mg.

After stirring 5 days in the cold, the latex-HCG reaction mixture was washed by membrane filtration in a Diaflo® filtration cell (max. capacity 65 ml) equipped with a white, plain Millipore filter (HA 0.45 u) using distilled water (doped with traces of toluene as preservative) under a nitrogen pressure of ≦3 p.s.i.g. at room temperature. The latex was washed with a total of 195 ml of water for 3.2 hours. The latex was removed from the cell via syringe and the cell was rinsed several times with 0.5–1 ml portions of water. The combined latex and rinses were treated with 1 ml each of Dowex® 50 × 8 (H+) and Dowex ® 1 × 8 (OH−) (both 30–50 mesh) in a 1 oz. stoppered siliconized bottle. The mixture was placed in a refrigerator and agitated gently at intermittent intervals for 2 hours. After settling the bulk of the latex was removed via a capillary syringe from the resin bed and the bed was rinsed with a little distilled water. Combined latex and rinse was centrifuged at low speed for several minutes and the latex was removed from a small amount of residual resin with a capillary syringe and dialyzed at 5° C in cellophane against 300 ml of pH 8.2, 0.1M glycine buffer for 24 hr. There was obtained 19.2 g of latex-HCG product containing 3.77% total solids and 2.14% polymer solids.

At 1:1 dilution with glycine buffer this latex-HCG preparation agglutinated within 1 min following admixture with 1 part Gravindex® HCG antiserum solution on a glass slide.

The following example illustrates the carboxylization of a uniform monodispersed styrene-acrylamide latex preparatory to the formation of the latex-antigen complex.

EXAMPLE 2

Styrene-acrylamide latex (50 ml) and 95% hydrazine (5 gr) were heated to 48°–52° C and stirred for 8 hours. When cooled the reaction mixture was transferred to a cellophane dialysis bag and dialyzed five times against 4 liters of deionized water. The dialysis bath was changed every 24 hours. Following the fifth dialysis the bath fluid was tested for the presence of unchanged hydrazine and found to be negative. The latex reaction mixture was dialyzed once more against 0.1 M sodium chloride to yield 82 grams of hydrazide styrene-acrylamide latex.

The hydrazide latex obtained above was treated while stirring, as previously, with 1.2 g of succinic anhydride in small portions during about 40 min, 1N NaOH being used to maintain a pH of about 4. After stirring for several hours, the latex's pH was lowered to about 3 and dialyzed against water under continuous flow for 3 days and statically for 6 days. Finally, the dialyzed latex was treated with 8 g (12 mequiv) of Dowex® 1 × 8 (20–50 mesh) resin in the OH form for 1.5 hours with intermittent mixing in a closed vessel and gravity filtered through a coarse sintered glass funnel. There was recovered 337 g of succinylhydrazide latex polymer (11.6%). By titration with standard NaOH the polymer was found to contain 0.095 mequiv of total —COOH per gram.

EXAMPLE 3

The succinylhydrazide styrene-acrylamide latex (3.9 grams, 0.45 grams of dry polymer, 0.043 mequiv —CO₂H) prepared in Example 2 above was mixed with 16 mg (0.11 m moles) of N-hydroxybenzotriazole dissolved in 0.4 ml of dimethylformamide diluted with 2 ml of water in a siliconized 25 ml round bottom flask containing a Teflon® stirring bar. The flask was cooled to 5° C and 1-cyclohexyl-3-(2-morpholinoethyl)-carbodiimide metho-p-toluenesulfonate (16 mg, 0.038 m mole) dissolved in 0.5 ml of water was added dropwise with vigorous stirring. Following the general procedure outlined in Example 1 above, the mixture was dialyzed, mixed with 5000 IU of HCG and stirred for 65 hours. Following membrane filtration and dialysis against glycine buffer (8.2 pH) 18.2 grams of the latex-HCG product was obtained.

When used in the indirect method for HCG diagnosis this preparation was capable of detecting between 12.5 and 25.0 IU/ml of HCG.

EXAMPLE 4

In a siliconized 50-ml round-bottomed flask containing a Teflon®-coated magnetic stirring bar a mixture was prepared containing 2.43 g (0.46 g polymer 0.11 mequiv —CO₂H) of monodispersed styrene-methacrylic acid latex suspension and a solution of 66 mg (0.65 mequiv) of N-hydroxypiperidine in 1 ml of water. This stirred mixture was immersed in an ice bath and when cooled to about 3°, a solution of 49 mg (0.12 mequiv) of 1-cyclohexyl-3-(2-morpholinoethyl)carbodiimide metho-p-toluenesulfonate in 1 ml of water was added. Stirring in the cold was continued for 3.5 hours whereupon the reaction mixture was transferred to a Diaflo® filtration cell which was equipped with a white, plain Millipore filter (HA 0.45 u) and cooled externally by an ice bath. The reaction mixture was then washed with 110 ml of cooled 0.1M NaCl under a nitrogen pressure ≦5 p.s.i.g. during 1.5 hours. The latex was removed from the filtration cell and the cell was washed vigorously three times (scattered larger particles of clumped latex were redispersed with the aid of a siliconized glass rod in a siliconized tube). The washed, cold latex mixture and rinses (approximately 20 ml) were combined in a clean 50-ml siliconized flask, treated with a cold solution of 5000 IU of HCG (Sigma Chem. Co., 5000 IU-vial containing lyophylized HCG, 50 mg of mannitol, 0.9% benzyl alcohol and phosphate buffer giving a pH of 7.2 in 10 ml of water) in 3 ml of distilled water containing 0.01% merthiolate. This mixture was stirred at about 5° for 3 days then centrifuged at 5° for 40 minutes at about 32,000xg. The supernatant was discarded and the latex residue was resuspended in 10 ml of pH 8.2 0.1M glycine buffer and filtered through a thin mat of glass wool. The centrifuge tube and mat were rinsed several times giving a latex-HCG preparation of 12 g, containing approximately 3.7% polymer solids.

This latex-HCG preparation was evaluated in an agglutination test on a glass slide with standard HCG antiserum solution and found to have a reciprocal antiserum endpoint of 20.

EXAMPLE 5

A siliconized 25-ml round-bottomed flask equipped with a Telfon®-coated magnetic stirring bar was charged with 2.43 g(0.46 g polymer; 0.11 mequiv — $CO_2H$) of styrene-methacrylic acid latex and a solution of 42 mg (0.42 mequiv) of 1-hydroxypiperidine in 1 ml of water. The resulting mixture was stirred and cooled in an ice bath. When cooled to about 2° the reaction mixture was treated with a solution of 47 mg (0.11 mequiv) of 1-cyclohexyl-3-(2-morpholinoethyl)carbodiimide metho-q-toluenesulfonate in 1 ml of water. The reaction mixture was stirred in the cold for 2 hours then diluted with 10 ml of cold 0.1M NaCl (0.01% merthiolate) and centrifuged at about 32,000 × g for 30 minutes at 5°. The supernatant solution was discarded and the polymer residue was resuspended in 7 ml of a cold solution of 5000 IU of HCG (lot 75C-0021) in 0.1M NaCl (0.01% merthiolate) and stirred at 5° for 6 days. The reaction mixture was diluted to 13.5 ml with pH 8.0 phosphate buffer and centrifuged as before. After discarding the supernatant the residue was resuspened in pH 8.2 glycine buffer and centrifuged again. The polymer residue was finally resuspended in about 10 ml of pH 8.2 glycine buffer and filtered through a small mat of glass wool. After rinsing the mat several times with buffer there was obtained 12.3 g of latex-HCG product.

This latex-HCG preparation had a reciprocal antiserum endpoint titer of 20 when diluted with glycine buffer containing 1% polyethylene glycol (MW 6000).

In carrying out the process described above a temperature of between 2° and 5° C is preferred for the reaction and workup. The final washing of the latex to remove unchanged protein may be done at room temperature for convenience but the product should be stored under refrigeration. Higher temperatures leads to side reactions and loss of activated ester. Lower temperatures will lead to freezing of the water in the latex and result in the destruction of the latex.

The preferred time for generation of the active ester is 3 to 5 hours. Longer generation times are inconsequential. Generally, 3 to 5 days is preferred for the coupling reaction to the protein. Longer times are inconsequential.

I claim:

1. A method for coupling a carboxylated latex to a protein with an amide bond which comprises reacting the latex with a water soluble carbodiimide and a water solubilized N-hydroxy compound to form an active ester latex, removing unchanged reactants from the active ester latex and coupling the cleaned active ester latex with a protein.

2. The method of claim 1 wherein the latex is a monodispersed uniform particle size latex selected from the group consisting of polymers ad copolymers containing acrylic acid, itaconic acid, fumaric acid, styrene, and methacrylic acid.

3. The method of claim 2 wherein the latex is reacted with an amount of the water-soluble carbodiimide equal to the chemical equivalence of the carboxyl groups of the latex for a period of from 3 to 5 hours at a temperature of from 2° to 5° C.

4. The method of claim 3 wherein the latex is styrene-acrylamide succinylhydrazide.

5. The method of claim 3 wherein the N-hydroxy compound is N-hydroxybenzotriazole.

6. The method of claim 4 wherein the protein is human chorionic gonadotropin.

* * * * *